(12) United States Patent
Hannon et al.

(10) Patent No.: US 11,744,693 B2
(45) Date of Patent: Sep. 5, 2023

(54) ESOPHAGEAL STENT INCLUDING A VALVE MEMBER

(71) Applicant: BOSTON SCIENTIFIC SCIMED, INC., Maple Grove, MN (US)

(72) Inventors: Michelle Hannon, Galway (IE); Nigel McMenamin, Galway (IE); Matthew Montague, Galway (IE); Michael G. Folan, Galway (IE); Alexandre Lambert, Bruyeres le Chatel (FR); Brian Joyce, Mayo (IE); Megan Niven, Minneapolis, MN (US); Allison M. Pearlman, Holden, MA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 477 days.

(21) Appl. No.: 16/596,061

(22) Filed: Oct. 8, 2019

(65) Prior Publication Data

US 2020/0030078 A1 Jan. 30, 2020

Related U.S. Application Data

(63) Continuation of application No. 15/450,636, filed on Mar. 6, 2017, now Pat. No. 10,456,237.

(Continued)

(51) Int. Cl.
*A61F 2/04* (2013.01)
*A61F 2/24* (2006.01)
(Continued)

(52) U.S. Cl.
CPC .............. *A61F 2/04* (2013.01); *A61F 2/2412* (2013.01); *A61F 2/2418* (2013.01); *A61F 2/958* (2013.01);
(Continued)

(58) Field of Classification Search
CPC ...... A61F 2/04; A61F 27/30; A61F 2002/044; A61F 2210/0014; A61F 2230/0021;
(Continued)

(56) References Cited

U.S. PATENT DOCUMENTS

| 6,503,272 B2 | 1/2003 | Duerig et al. |
| 6,790,237 B2 | 9/2004 | Stinson |

(Continued)

FOREIGN PATENT DOCUMENTS

| JP | 2005052419 A | 3/2005 |
| JP | 2009520559 A | 5/2009 |
| WO | 2007072469 A2 | 6/2007 |

OTHER PUBLICATIONS

"ALIMAXX-ES Fully Covered Esophageal Stent," Meritmedical Endotek, pp. 1-2, 2010.

(Continued)

*Primary Examiner* — Keri J Nelson
*Assistant Examiner* — Aren Patel
(74) *Attorney, Agent, or Firm* — Seager, Tufte & Wickhem, LLP

(57) ABSTRACT

An example medical device is disclosed. The example medical device includes a tubular scaffold. The scaffold includes a longitudinal axis, an inner surface and an outer surface. The medical device also includes a flexible valve extending radially inward from the inner surface of the scaffold. The valve includes an annular chamber extending circumferentially around the inner surface of the scaffold and is configured to shift from a closed configuration to an open configuration.

20 Claims, 18 Drawing Sheets

Related U.S. Application Data

(60) Provisional application No. 62/304,739, filed on Mar. 7, 2016.

(51) Int. Cl.
    *A61F 2/958* (2013.01)
    *A61L 27/02* (2006.01)
    *A61L 27/56* (2006.01)
    *A61L 27/30* (2006.01)
    *B05D 1/02* (2006.01)
    *A61L 27/36* (2006.01)

(52) U.S. Cl.
    CPC .............. *A61L 27/025* (2013.01); *A61L 27/30* (2013.01); *A61L 27/56* (2013.01); *B05D 1/02* (2013.01); *A61F 2002/044* (2013.01); *A61F 2210/0014* (2013.01); *A61F 2210/0076* (2013.01); *A61F 2230/0021* (2013.01); *A61F 2230/0067* (2013.01); *A61L 27/3679* (2013.01)

(58) Field of Classification Search
    CPC ........... A61F 2230/0067; A61L 27/025; A61L 27/56; A61L 27/3679; B05D 1/02
    See application file for complete search history.

(56) References Cited

U.S. PATENT DOCUMENTS

| | | | |
|---|---|---|---|
| 7,354,455 B2 | 4/2008 | Stinson | |
| 8,603,188 B2 | 12/2013 | Behan et al. | |
| 8,603,189 B2 | 12/2013 | Behan et al. | |
| 8,932,346 B2 | 1/2015 | Kuehling et al. | |
| 8,986,368 B2 | 3/2015 | Gill et al. | |
| 2001/0010012 A1* | 7/2001 | Edwin | A61F 2/90 623/1.13 |
| 2003/0208261 A1 | 11/2003 | Thorpe et al. | |
| 2004/0243219 A1 | 12/2004 | Fischer et al. | |
| 2007/0112437 A1 | 5/2007 | Shank | |
| 2008/0281409 A1 | 11/2008 | Malone et al. | |
| 2008/0312735 A1 | 12/2008 | Thorpe et al. | |
| 2010/0114327 A1 | 5/2010 | Sobrino-Serrano | |
| 2010/0121461 A1 | 5/2010 | Sobrino-Serrano et al. | |
| 2010/0256776 A1 | 10/2010 | Levine et al. | |
| 2011/0160836 A1 | 6/2011 | Behan | |
| 2011/0307070 A1 | 12/2011 | Clerc et al. | |
| 2012/0059486 A1 | 3/2012 | Sobrino-Serrano et al. | |
| 2012/0123195 A1 | 5/2012 | Woodruff et al. | |
| 2013/0006382 A1 | 1/2013 | Behan | |
| 2013/0110253 A1 | 5/2013 | Gill et al. | |
| 2013/0289711 A1* | 10/2013 | Liddy | A61F 2/06 623/1.24 |
| 2013/0325141 A1 | 12/2013 | Gill et al. | |
| 2013/0345786 A1 | 12/2013 | Behan | |
| 2014/0031951 A1* | 1/2014 | Costello | A61F 2/04 623/23.68 |
| 2014/0114432 A1 | 4/2014 | Shalon | |
| 2014/0173878 A1* | 6/2014 | Merk | A61F 2/95 29/446 |
| 2014/0243950 A1 | 8/2014 | Weiner | |
| 2014/0257461 A1 | 9/2014 | Robinson et al. | |
| 2014/0277573 A1 | 9/2014 | Gill et al. | |
| 2015/0045908 A1* | 2/2015 | McMahon | A61F 2/90 623/23.68 |
| 2015/0173919 A1* | 6/2015 | Baldwin | C23C 16/513 29/446 |
| 2015/0190220 A1 | 7/2015 | Gill et al. | |
| 2017/0049590 A1* | 2/2017 | Hingston | B29C 53/60 |
| 2017/0151049 A1* | 6/2017 | La Francesca | A61F 2/04 |
| 2018/0274131 A1* | 9/2018 | Naz | A61L 31/10 |

OTHER PUBLICATIONS

International Search Report and Written Opinion dated Jun. 9, 2017 for International Application No. PCT/US2017/020955.

* cited by examiner

ESOPHAGEAL STENT INCLUDING A VALVE MEMBER

CROSS-REFERENCE TO RELATED APPLICATIONS

This application is a continuation of U.S. patent application Ser. No. 15/450,636, filed Mar. 6, 2017, which claims priority to U.S. Provisional Patent Application Ser. No. 62/304,739, filed on Mar. 7, 2016, the contents of which are fully incorporated herein by reference.

TECHNICAL FIELD

The present disclosure pertains to medical devices, and methods for manufacturing medical devices. More particularly, the present disclosure pertains to stents including a valve, such as an anti-reflux valve, and methods for manufacturing and using such stents.

BACKGROUND

The lower esophageal sphincter is a muscle located between the esophagus and the stomach. The sphincter normally functions as a one-way valve, allowing material (e.g., food) that travels downward through the esophagus to enter the stomach while preventing the backflow (reflux) of hydrochloric acid and other gastric contents into the esophagus. However, in some cases the lower esophageal sphincter does not close adequately, and therefore, permits stomach acid to reflux into the esophagus, causing heartburn. A weak or inoperable lower esophageal sphincter is a major cause of gastroesophageal reflux disease (GERD).

Therefore, a variety of intracorporeal medical devices have been developed to treat gastroesophageal disease caused by a malfunctioning lower esophageal sphincter. For example, elongated stents incorporating one-way valves have been developed to allow material (e.g., food) to travel through the esophagus and enter the stomach while also preventing stomach acid to reflux into the esophagus. However, there is an ongoing need to provide alternative configurations of and/or methods of forming stents including a one-way valve to treat gastroesophageal disease, as well as other medical conditions.

BRIEF SUMMARY

This disclosure provides design, material, manufacturing method, and use alternatives for medical devices. An example medical device includes a tubular scaffold. The scaffold includes a longitudinal axis, an inner surface and an outer surface. The medical device also includes a flexible valve extending radially inward from the inner surface of the scaffold. The valve includes an annular chamber extending circumferentially around the inner surface of the scaffold and is configured to shift from a closed configuration to an open configuration.

Alternatively or additionally to any of the embodiments above, wherein the valve includes a first end and a second end, the first end spaced along the longitudinal axis from the second end, and wherein the chamber is positioned between the first end and the second end.

Alternatively or additionally to any of the embodiments above, wherein the valve narrows from the first end to the second end.

Alternatively or additionally to any of the embodiments above, wherein the valve further includes a first wall thickness adjacent the first end and a second wall thickness adjacent the second end, and wherein second wall thickness is thicker than the first wall thickness.

Alternatively or additionally to any of the embodiments above, further comprising an inner layer disposed along the inner surface of the scaffold, and wherein the valve is formed from at least a portion of the inner layer.

Alternatively or additionally to any of the embodiments above, further comprising an outer layer disposed along the outer surface of the scaffold, and wherein the annular chamber is defined between the inner layer and the outer layer.

Alternatively or additionally to any of the embodiments above, further comprising an inner layer disposed along the inner surface of the scaffold and an outer layer disposed along the outer surface of the scaffold, wherein the inner layer is circumferentially attached at a first location and a second location, wherein the outer layer extends at least between the first location and the second location, and wherein the annular chamber is defined between the inner layer and outer layer.

Alternatively or additionally to any of the embodiments above, wherein the medical device includes at least one aperture extending through the outer layer, the inner layer or both the inner and outer layers.

Alternatively or additionally to any of the embodiments above, wherein the chamber is substantially air-filled.

Alternatively or additionally to any of the embodiments above, wherein the chamber is filled with a material selected from the group comprising liquids, gels, foams and polymers.

Alternatively or additionally to any of the embodiments above, wherein at least a portion of the valve includes a surface texture configured to prohibit material from moving through the valve in a retrograde direction.

Alternatively or additionally to any of the embodiments above, wherein at least a portion of the valve includes a coating comprising one or more acid neutralizers.

Alternatively or additionally to any of the embodiments above, wherein the medical device includes a second valve.

Alternatively or additionally to any of the embodiments above, further comprising a coating applied to the valve, wherein the coating is configured to minimize the surface friction of the valve.

Alternatively or additionally to any of the embodiments above, wherein the coating is a silicone coating.

An esophageal stent includes an expandable tubular scaffold. The scaffold includes a longitudinal axis and an inner surface. The stent also includes a valve positioned on the inner surface of the scaffold, the valve including a first end and a second end. The valve is configured to funnel material along the longitudinal axis and to radially expand from a closed configuration to an open configuration.

Alternatively or additionally to any of the embodiments above, wherein the valve includes a widened portion adjacent the first end of the valve and a closed portion adjacent the second end of the valve.

Alternatively or additionally to any of the embodiments above, wherein the valve narrows from the widened portion to the closed portion.

Alternatively or additionally to any of the embodiments above, wherein the valve further defines an annular chamber extending circumferentially around the inner surface of the scaffold.

Alternatively or additionally to any of the embodiments above, wherein the chamber is filled with a material selected from the group comprising liquids, gels and polymers.

Alternatively or additionally to any of the embodiments above, further comprising an inner layer extending from a first end of the stent to a second end of the stent, and wherein the valve is formed from at least a portion of the inner layer.

An example esophageal stent for treating acid reflux includes an expandable tubular member. The tubular member includes a longitudinal axis and an inner surface. The stent also includes a valve positioned on the inner surface of the scaffold. The valve includes an annular chamber extending circumferentially around the inner surface of the tubular member. The valve is configured to funnel material along the longitudinal axis and to permit material to pass through the valve in a first direction and to prevent material from passing through the valve a second direction, wherein the first direction is opposite the second direction.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
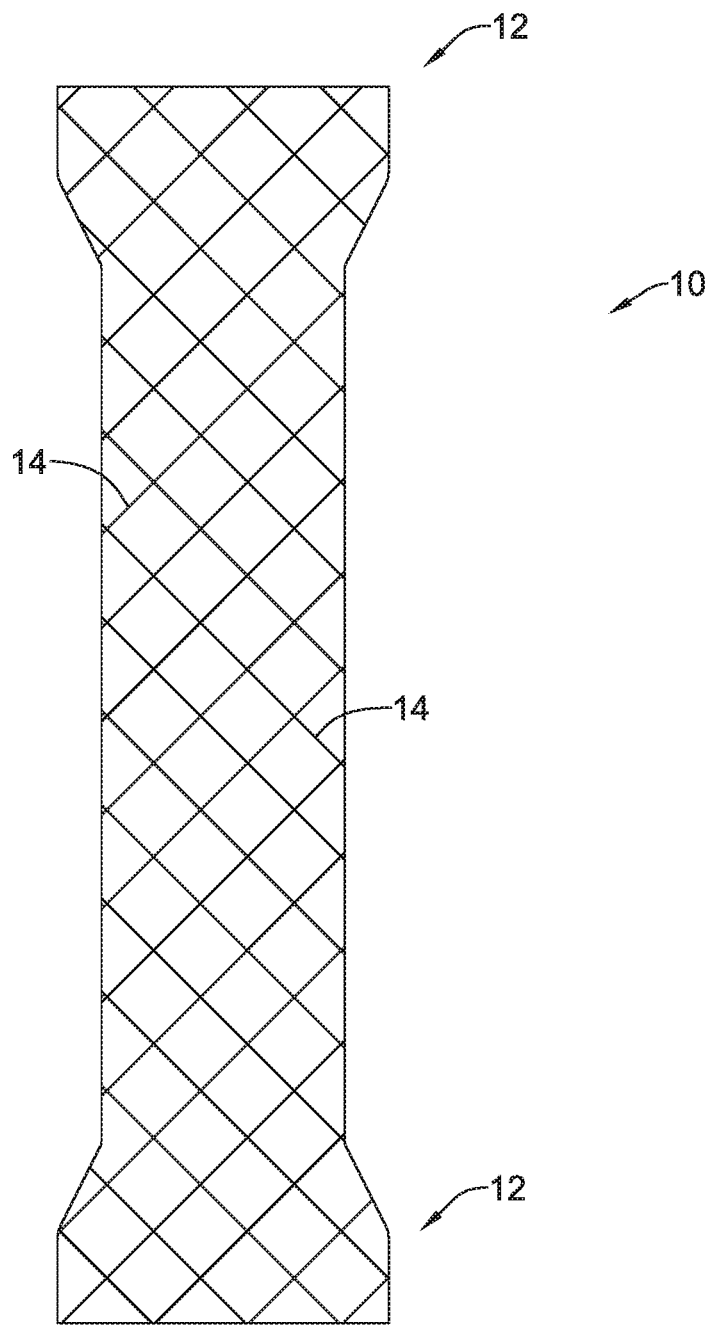
FIG. 1 is an example stent.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

Gastroesophageal reflux disease (GERD) is a medical condition whereby stomach acids enter the lower portion of the esophagus because the lower esophageal sphincter (positioned at the entrance of the stomach) fails to close properly. In some instances, the lower esophageal sphincter's inability to close is due to disease or general atrophy. When left open, the sphincter may permit reflux of stomach acids into the esophagus, causing severe heartburn and potentially contributing to the onset of other diseases.

One method of treating GERD is to place an anti-reflux stent into the entrance of the stomach. An anti-reflux stent may include an expandable valve which allows food and liquid to enter the stomach but prevents liquids from passing back through the valve. In general, there is an ongoing need for an anti-reflux stent to provide a smooth lumen opening into the stomach while preventing stomach acids from passing back through the valve and into the esophagus.

FIG. 1 shows an example stent 10. Stent 10 may include one or more stent strut members 14. Stent strut members 14 may extend longitudinally along stent 10. While FIG. 1 shows stent strut members 14 extending along the entire length of stent 10, in other examples, the stent strut members 14 may extend only along a part of stent 10.

Additionally, FIG. 1 shows example stent 10 including one or more flared end portions 12 proximate the first and second ends of the stent 10. In some instances, flared portion 12 may be defined as an increase in the outer diameter, the inner diameter or both the inner and outer diameter along one or both of the end portions 12 of stent 10.

In some instances, stent 10 may be a self-expanding stent or stent 10 may be a balloon expandable stent. Self-expanding stent examples may include stents having one or more struts 14 combined to form a rigid and/or semi-rigid stent structure. For example, stent struts 14 may be wires or filaments braided, intertwined, interwoven, weaved, knitted or the like to form the stent structure. Alternatively, stent 10 may be a monolithic structure formed from a cylindrical tubular member, such as a single, cylindrical tubular laser-cut Nitinol tubular member, in which the remaining portions of the tubular member form the stent struts 14. Openings or interstices through the wall of the stent 10 may be defined between adjacent stent struts 14.

Stent 10 in examples disclosed herein may be constructed from a variety of materials. For example, stent 10 (e.g., self-expanding or balloon expandable) may be constructed from a metal (e.g., Nitinol). In other instances, stent 10 may be constructed from a polymeric material (e.g., PET). In yet other instances, stent 10 may be constructed from a combination of metallic and polymeric materials. Additionally, stent 10 may include a bioabsorbable and/or biodegradable material.

Figure 2:
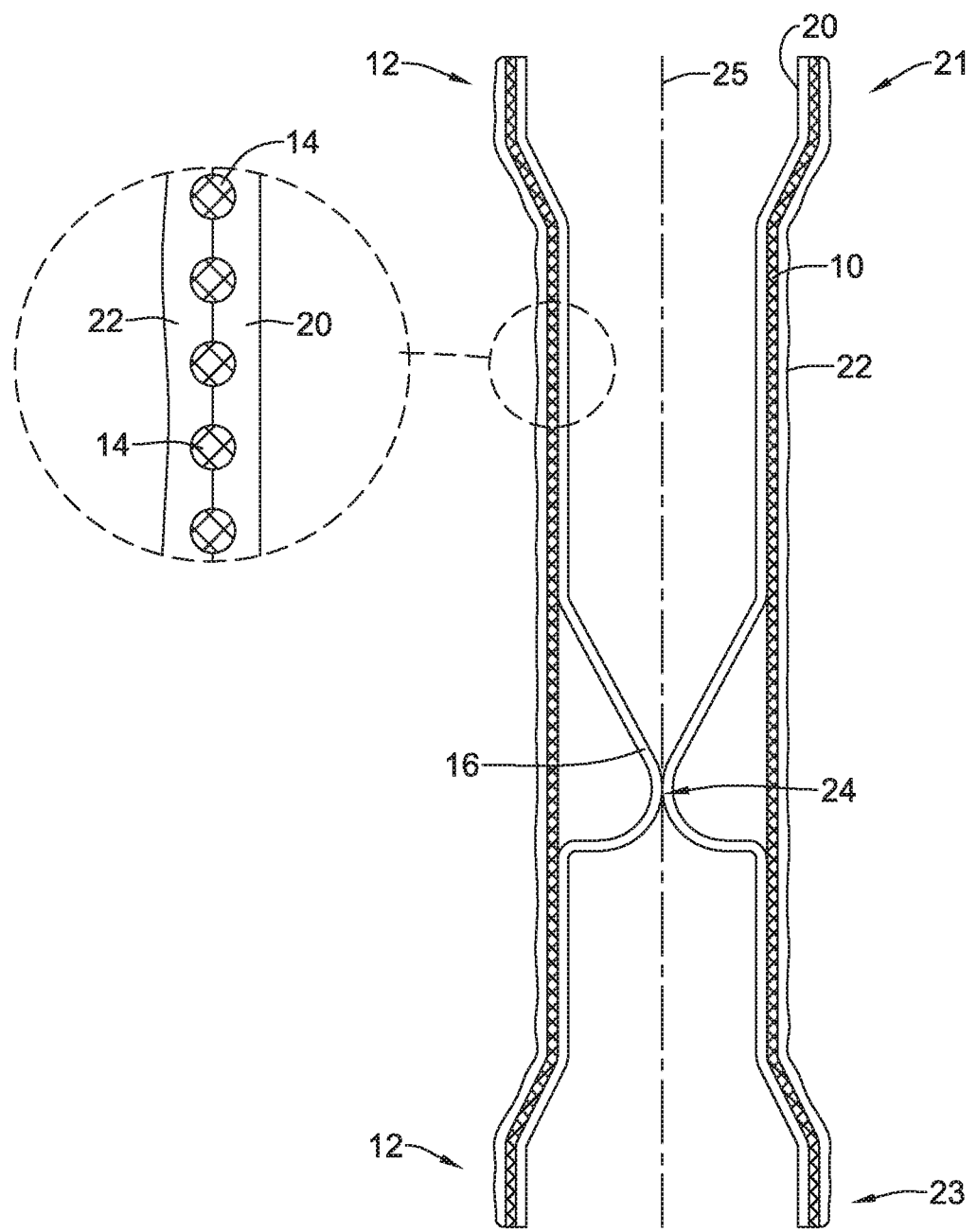
FIG. 2 is a cross-sectional view of the stent of FIG. 1 including a valve.

In some instances, example stent 10 may include one or more layers positioned on and/or adjacent to the outer surface of stent 10. For example, FIG. 2 shows example stent 10 including an outer layer 22 disposed along the outer surface of stent 10. In some instances, outer layer 22 may be an elastomeric or non-elastomeric material. For example, outer layer 22 may be a polymeric material, such as silicone, polyurethane, or the like. Further, the outer layer 22 may span the spaces (e.g., openings, cells, interstices) in the wall of stent 10. For example, FIG. 2 shows outer layer 22 extending inwardly from the outer surface of stent 10 such that the outer layer 22 spans one or more of spaces (e.g., openings, cells, interstices) between struts 14 in the wall of stent 10.

Additionally, example stent 10 may include one or more layers positioned on and/or adjacent to the inner surface of stent 10. FIG. 2 shows example stent 10 including an inner layer 20 disposed along the inner surface of stent 10. In some instances, inner layer 20 may be an elastomeric or non-elastomeric material. For example, inner layer 20 may be a polymeric material, such as silicone, polyurethane, or the like. Further, the inner layer 20 may span the spaces (e.g., openings, cells, interstices) in the wall of stent 10. For example, FIG. 2 shows inner layer 20 extending outwardly from the inner surface of stent 10 such that the inner layer 22 spans one or more of spaces (e.g., openings, cells, interstices) between struts 14 in the wall of stent 10.

It can be appreciated that as inner layer 20 and outer layer 22 extend outwardly and inwardly, respectively, they may touch and/or form an interface region within the spaces (e.g., openings, cells, interstices) in the wall of stent 10. For example, the detailed view of FIG. 2 shows that both the inner and outer layers 20/22 may extend into the openings defined between adjacent stent struts 14 and form an interface region. Further, the inner and outer layers 20/22 may additionally extend between adjacent struts 14, thereby filling any space between adjacent strut members 14.

As shown in FIG. 2, stent 10 may have a first end 21 and a second end 23. When positioned in a body lumen (e.g., esophagus) first end 21 may be defined as the end of stent 10 closest to a patient's mouth and second end 23 may be defined as the end of stent 10 closest to a patient's stomach.

As shown in FIG. 2, inner layer 20 and outer layer 22 may extend along the length of stent 10 from first end 21 to second end 23. In other words, in some instances inner layer 20 and outer layer 22 may be defined as continuous layers that extend from first end 21 to second end 23 of stent 10. However, in other instances inner layer 20 and/or outer layer 22 may extend less than the entire length of stent 10, if desired.

Additionally, FIG. 2 shows valve member 16 positioned within the lumen of stent 10. As will be discussed in greater detail below, valve 16 may be defined as a portion of inner layer 20. In other words, valve 16 may be a unitary structure formed in conjunction with inner layer 20. For example, FIG. 2 illustrates that valve 16 may be an inwardly extending portion of inner layer 20. In other words, valve 16 may be defined as a unitary portion of inner layer 20 that extends radially inward from an inner surface of stent 10 toward the central longitudinal axis 25 of stent 10.

Further, in some examples, valve 16 may be defined as a portion of inner layer 20 that extends circumferentially within the lumen of stent member 10. In other words, it can be appreciated that valve 16 may be defined as an annular member that extends continuously around the lumen of stent member 10. Further, valve 16 may be defined as an uninterrupted extension of inner layer 20 projecting toward central longitudinal axis 25.

As will be discussed in further detail below, FIG. 2 illustrates that valve 16 may include a conical wall and generally be shaped to taper longitudinally from the portion of valve 16 closest to first end 21 to the portion of valve 16 closest to second end 23. For example, the wall of valve 16 illustrated in FIG. 2 may bear some resemblance to a cone-shaped funnel tapering from a wide portion nearest a patient's mouth to a narrow portion nearest a patient's stomach. Further, as illustrated in FIG. 2, valve 16 may taper inwardly toward central longitudinal axis 25 and close (e.g., contact, seal, etc.) onto itself such that it stops flow of material (e.g., stomach acid) from flowing through the lumen of stent 10. As discussed above, it may be desirable for valve 16 to prevent stomach acids from flowing from a patient's stomach toward the patient's mouth. FIG. 2 shows valve 16 in a closed portion 24.

However, in some instances it may be desirable for valve 16 to expand radially outward to permit nutritional material to pass through the lumen of stent 10. For example, in some examples it is desirable for valve 16 to radially expand to permit food to pass from a patient's mouth, through the valve 16, to the stomach.

Figure 3:
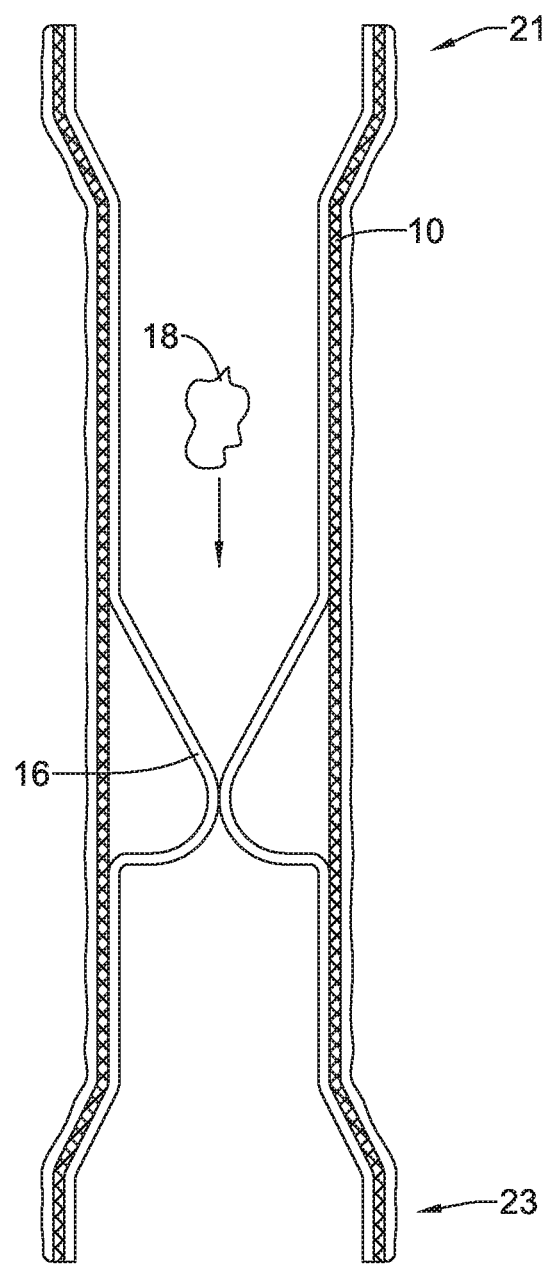
FIGS. 3 and 4 are cross-sectional views of the stent of FIG. 1 illustrating material passing through the valve.
Figure 4:
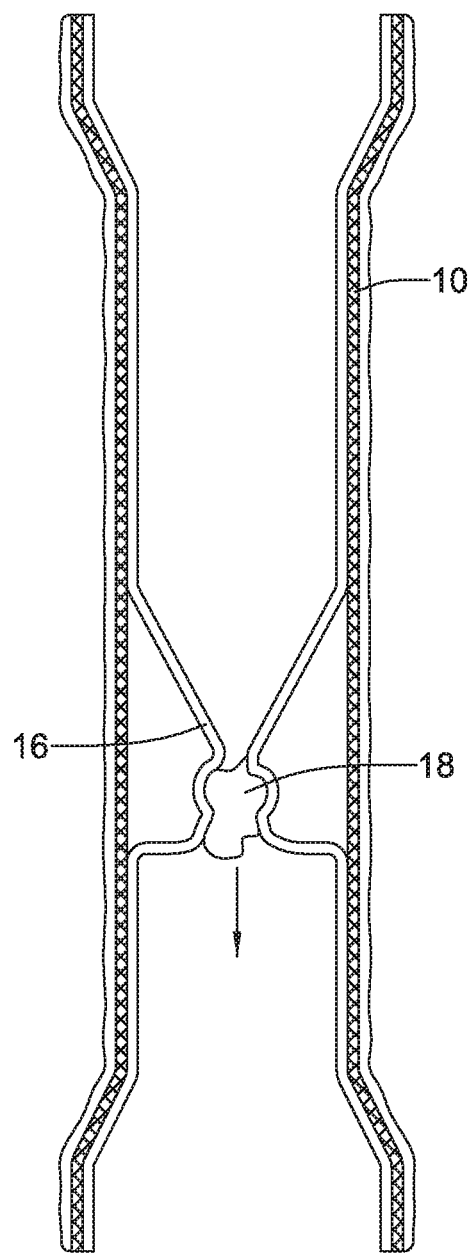

FIGS. 3 and 4 illustrate valve 16 expanding radially outward to allow nutritional material (e.g., food) to pass through the lumen of stent 10. As shown by the arrow in FIG. 3, and, in general, nutritional material 18 may flow through stent 10 from a first end 21 (e.g., the end closest to a patient's mouth) to a second end 23 (e.g., the end closest to a patient's stomach). FIG. 4 illustrates that valve 16 may permit the material 18 to pass through the lumen of the stent 10 by expanding radially outward as the material 18 passes through the valve 16. As shown in FIG. 4, in some instances, the valve 16 may conform to the shape of material 18 as it passes through the valve 16.

Figure 5:
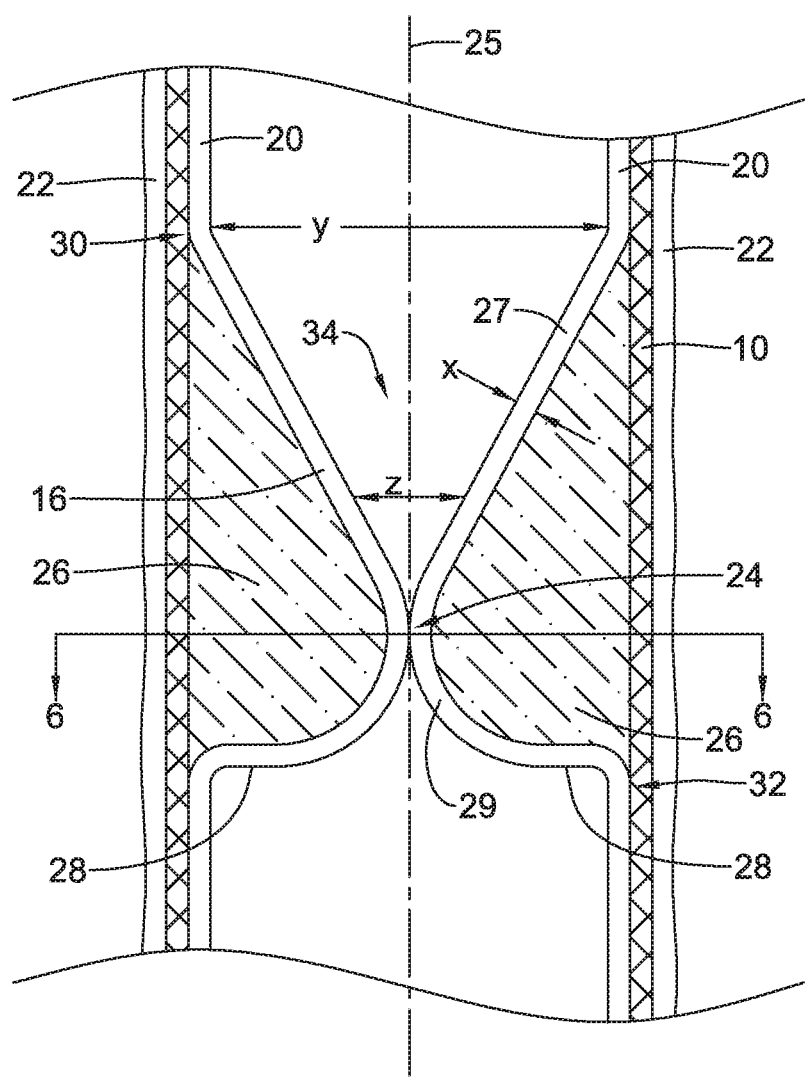
FIG. 5 is an enlarged cross-sectional view of a portion of the stent of FIG. 1 including the valve in a closed configuration.

FIG. 5 illustrates an example stent 10 including valve member 16. As described above, stent 10 may include an outer layer 20 and inner layer 22. Further, valve 16 may be defined by inner layer 22. For example, FIG. 5 illustrates that inner layer 20 may include a thickness depicted as "X." It can be appreciated that thickness "X" may be defined as depth to which inner layer 20 extends radially inward from the inner surface of stent member 10. In some examples, the inner layer 22 may be formed from a silicone material.

FIG. 5 is an enlarged view of the valve 16 within the lumen of the stent 10. As shown in FIG. 5, the inner layer 22 may separate from the inner surface of stent member 10 at two or more locations. For example, FIG. 5 shows a first detachment point 30 and a second detachment point 32. It is noted that detachment points 30/32 are circumferential lines extending around the circumference of stent 10 where the inner layer 22 moves away from the inner surface of the wall of the stent 10 as the inner layer 22 moves radially inward toward the longitudinal axis 25 to form valve 16. Detachment points 30/32 may be defined as locations at which the outer surface of the inner layer 20 separates from the inner surface of stent member 10. It can be appreciated that this location may also be defined as the location at which inner layer 20 defines a wall having a "wall thickness" defining valve 16.

FIG. 5 shows that in some instances the wall thickness of valve 16 may be substantially equal to the thickness "X" of inner layer 20. In other words, inner layer 20 may maintain a substantially uniform wall thickness along the length of stent member 10 (including the wall thickness of valve 16). However, as will be discussed in more detail below, in other embodiments the thickness of inner layer 20, outer layer 22 and/or the wall thickness defining valve 16 may change along any portion of stent member 10. For example, some portions of inner layer 20, outer layer 22 and/or the wall thickness defining valve 16 may be thinner or thicker than other portions along stent member 10.

As discussed above, inner layer 20 may separate from the inner surface of stent member 10 at first and second detachment points 30/32 and be located radially inward and unattached to the inner surface of stent 10 between first and second detachment points 30/32. Further, FIG. 5 illustrates that the separation of inner layer 22 from the inner surface of stent member 10 defines a valve 16 having a wall thickness "X." Further yet, FIG. 5 illustrates a "chamber" 26 (e.g., sac, cavity, void, pocket, enclosure, etc.) which may be defined as the space between the valve wall and stent member 10 (which may include outer layer 22) between detachment points 30/32. Chamber 26 may be positioned between detachment points 30/32. In FIG. 5, the chamber 26 is depicted with a hash-mark pattern for reference. Thus, chamber 26 may be defined as a space between the wall of the stent 10 (including outer layer 22) and the wall of the valve 16 (formed by the inner layer 20) between the circumferential detachment points 30/32.

Similarly to the above discussion regarding the wall of valve 16, chamber 26 may be defined as extending circumferentially within the lumen of stent member 10. In other words, it can be appreciated that chamber 26 may be defined as an annular cavity that extends continuously around the lumen of stent member 10 radially inward of the stent wall. Further, it can be appreciated the shape of chamber 26 is directly related to the shape of the wall of valve 16. In other words, in some instances the shape of valve 16 may define the shape of chamber 26.

In some instances, chamber 26 may be filled with variety of materials. For example, chamber 26 may be filled with a fluid (e.g., a gas, air, liquid, gel or any other similar material). In some instances, chamber 26 may be filled with saline, gel or air. In other instances, chamber 26 may be filled with a foam material, such as an open-cell foam or a closed-cell foam, which may be readily compressible and recoverable to its original shape. As described above, in some instances it may be desirable for valve 16 to expand radially outward (e.g., as food passes through the valve), and therefore, it may be desirable to fill chamber 26 with a material that is compressible, displaceable and/or able to move in response to a variety of forces placed thereon.

In other instances chamber 26 may only contain air or another type of gas. Similar to that described above, a gas-filled chamber 26 may be able to expand radially outward (e.g., as food passes through the valve), and therefore, it may be desirable to fill chamber 26 with a gas at a pressure that allows the valve 16 to move in response to a variety of forces placed thereon.

Similarly to the example shown in FIG. 2, the valve 16 illustrated in FIG. 5 may bear some resemblance to a cone-shaped funnel. For example, the radially inward surface of the wall of valve 16 may taper radially inward from detachment point 30 to closure point 24. Additionally, FIG. 5 shows valve 16 including a tapered wall portion 27 extending from detachment point 30 toward central longitudinal axis 25. Further, valve 16 may include a wide portion (depicted in FIG. 5 as dimension "Y") tapering to a narrower portion (depicted in FIG. 5 as dimension "Z"). As shown in FIG. 5, the wide portion of valve 16 may be positioned adjacent to first detachment point 30, while the narrower portion may be positioned closer to closure point 24. Further, as described above with respect to FIG. 2, the continuous, circumferential (e.g., annular) shape of valve 16 may define a funnel-shaped portion 34.

Additionally, valve 16 may include a rounded portion 29 and a downward-facing portion 28. For simplicity purposes, the term "downward-facing" is used herein to generally describe portions of valve 16 which face toward the stomach distal of closure point 24. As illustrated in FIG. 5, rounded portion 29 is positioned between tapered portion 27 and downward-facing portion 28. In other words, in some examples, valve 16 may be defined as including tapered portion 27, rounded portion 29, and downward-facing portion 28 (which terminates at second detachment point 32). In some instances, tapered portion 27 begins to taper at a point adjacent to first detachment point 30. Downward-facing portion 28 may extend from rounded portion 29 to second detachment point 32. In some examples, closure point 24 may be located along a portion of rounded portion 29. Closure point 24 may be located between first and second detachment points 30/32 proximate central longitudinal axis 25. For example, closure point 24 may be at central longitudinal axis 25.

Additionally, FIG. 5 shows outer layer 22 extending along stent 10 for the entire length of valve 16. In other words, stent 10 may include outer layer 22 extending from at least detachment point 30 to detachment point 32. However, in some examples, outer layer 22 may extend the entire length of stent 10, while in other instances outer layer 22 may not extend the entire length of stent 10. In some examples, the outer layer 22 may be configured to prevent cellular ingrowth. For instance, in some examples outer layer 22 may include a polymeric material, such as polyurethane or silicone (e.g., high durometer silicone) to resist cellular ingrowth. The radially outward extent of chamber 26 may be bounded by outer layer 22, whereas the radially inward extent of chamber 26 may be bounded by inner layer 20.

Figure 6:
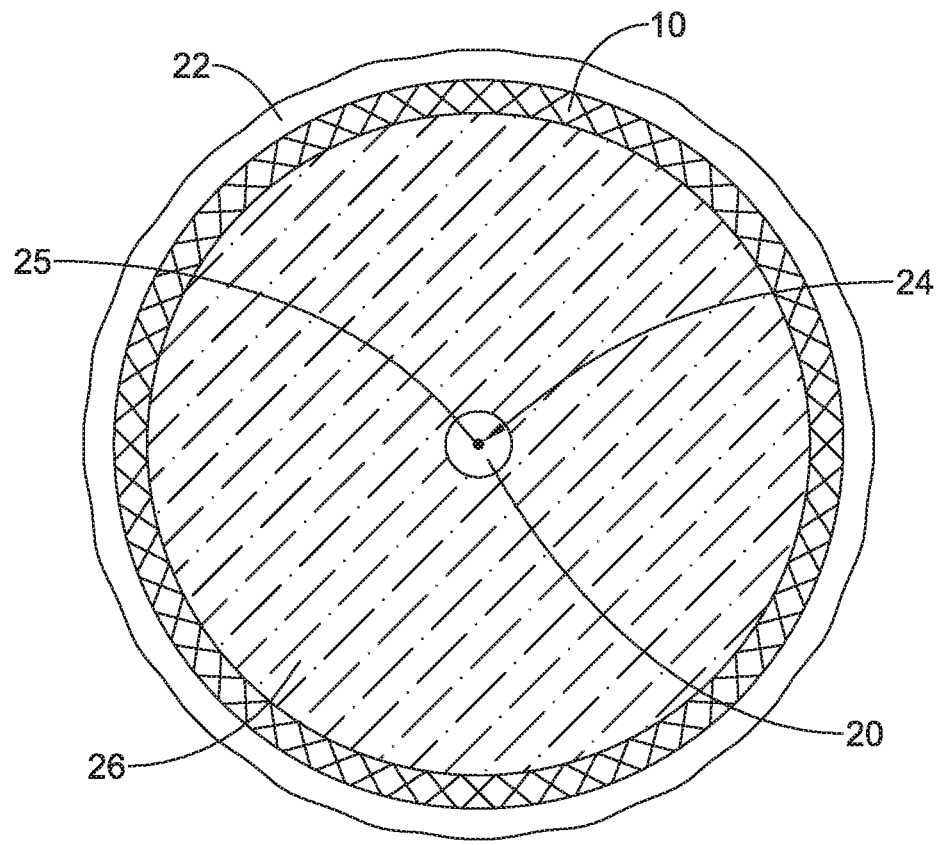
FIG. 6 is a cross-sectional view of the stent and valve of FIG. 5 taken along line 6-6 of FIG. 5.

FIG. 6 shows a cross-sectional view along line 6-6 of FIG. 5. In particular, line 6-6 of FIG. 5 intersects closure point 24 described above. Therefore, as shown in FIG. 6, closure point 24 is positioned in the center of the lumen of stent 10. Further, FIG. 6 shows outer layer 22, stent 10, chamber 26 and inner layer 20. Additionally, FIG. 6 illustrates that chamber 26 and inner layer 20 extend circumferentially around the central longitudinal axis 25 (which coincides with closure point 24 in FIG. 6). As described above, FIG. 6 shows that chamber 26 and inner layer 20 (defining the wall of valve 16), extend continuously around the central longitudinal axis 25. As noted above, the radially outward extent of chamber 26 may be bounded by outer layer 22 and the radially inward extent of chamber 26 may be bounded by inner layer 20.

Figure 7:
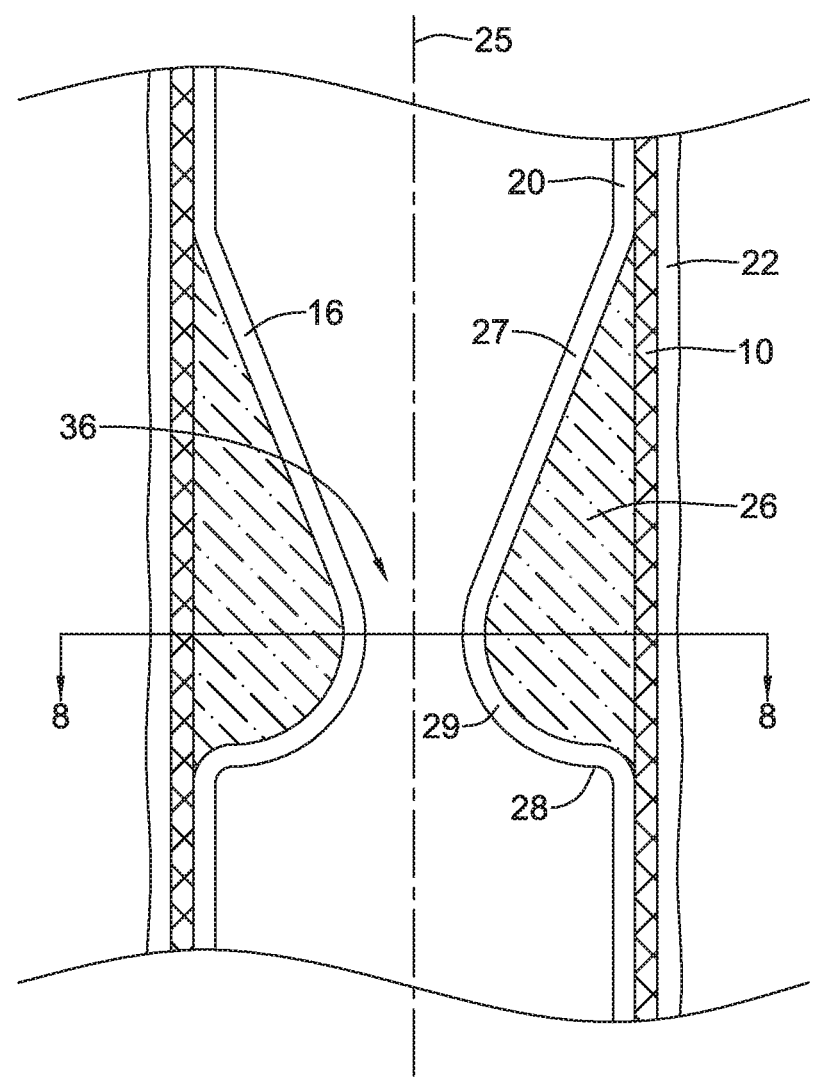
FIG. 7 is a cross-sectional view of another example valve positioned in a stent.

FIG. 7 shows an example stent 10 including features and/or elements similar to those described above. For example, FIG. 7 shows a valve 16 including stent 10, outer layer 22, and inner layer 22 defining tapered conical portion 27, rounded portion 29 and downward-facing portion 28. Additionally, valve 16 defines chamber 26 extending between first detachment point 30 and second detachment point 32 and bounded by the inner layer 20 and the outer layer 22. Namely, the radially outward extent of chamber 26 may be bounded by outer layer 22 and the radially inward extent of chamber 26 may be bounded by inner layer 20. However, the configuration of valve 16 in FIG. 7 does not include a closure point. Rather, FIG. 7 shows that in some instances while tapered portion 27 of valve 16 tapers radially inward towards the central longitudinal axis 25, it does not form a closure point 24. Rather, FIG. 7 shows that in some examples valve 16 includes a valve opening 36 located at the central longitudinal axis 25.

Figure 8:
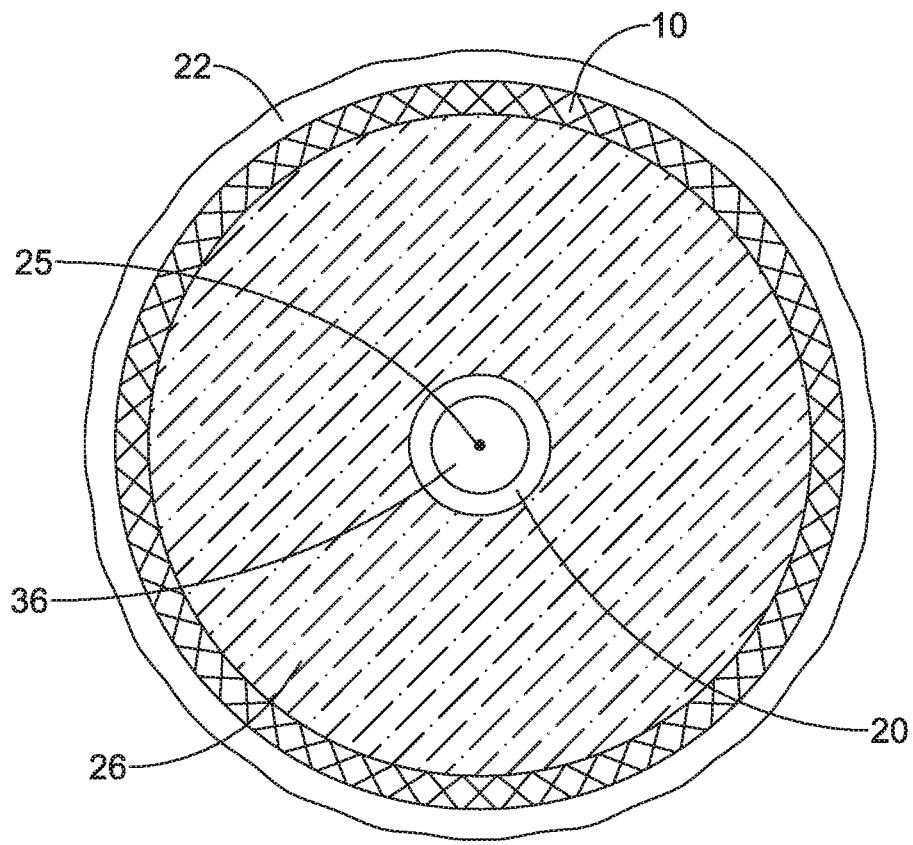
FIG. 8 is a cross-sectional view of the stent and valve of FIG. 7 taken along line 8-8 of FIG. 7.

FIG. 8 shows a cross-sectional view of the example stent 10 and valve 16 depicted in FIG. 7. The cross-section shown in FIG. 8 is taken along line 8-8 of FIG. 7. Line 8-8 of FIG. 7 transects the valve opening 36 described above. As noted above, the radially outward extent of chamber 26 may be bounded by outer layer 22 and the radially inward extent of chamber 26 may be bounded by inner layer 20. As shown in FIG. 8 (and contrasted with the example valve shown in FIG. 6), valve opening 36 may be defined as an aperture and/or opening centered about the central longitudinal axis 25 of the lumen of stent 10. However, while the figures described herein depict example valves and related elements centered about the central longitudinal axis, it is contemplated that any of the examples described herein may be designed such that the structural elements defining any portion of stent 10 and/or valve 16 may be off-center. In other words, valve 16 may be asymmetrical about the central longitudinal axis 25 in one or more examples described herein.

Figure 9:
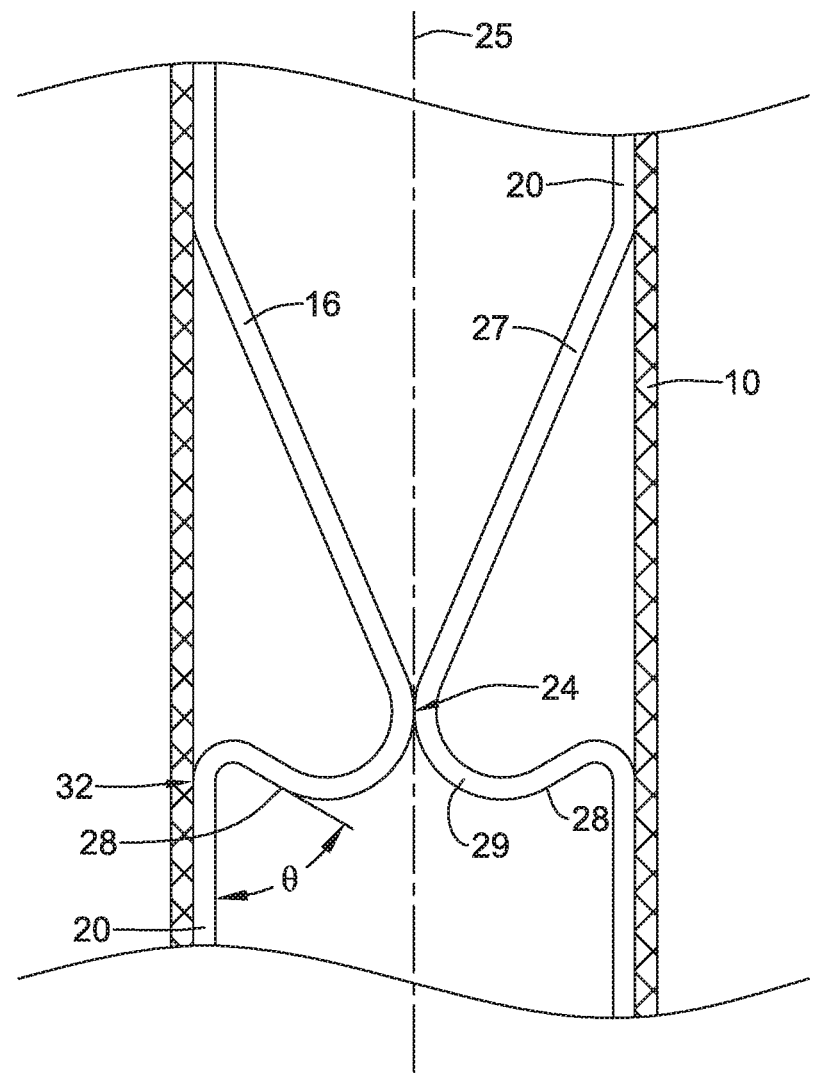
FIG. 9 is a cross-sectional view of an example stent and valve configuration.
Figure 10:
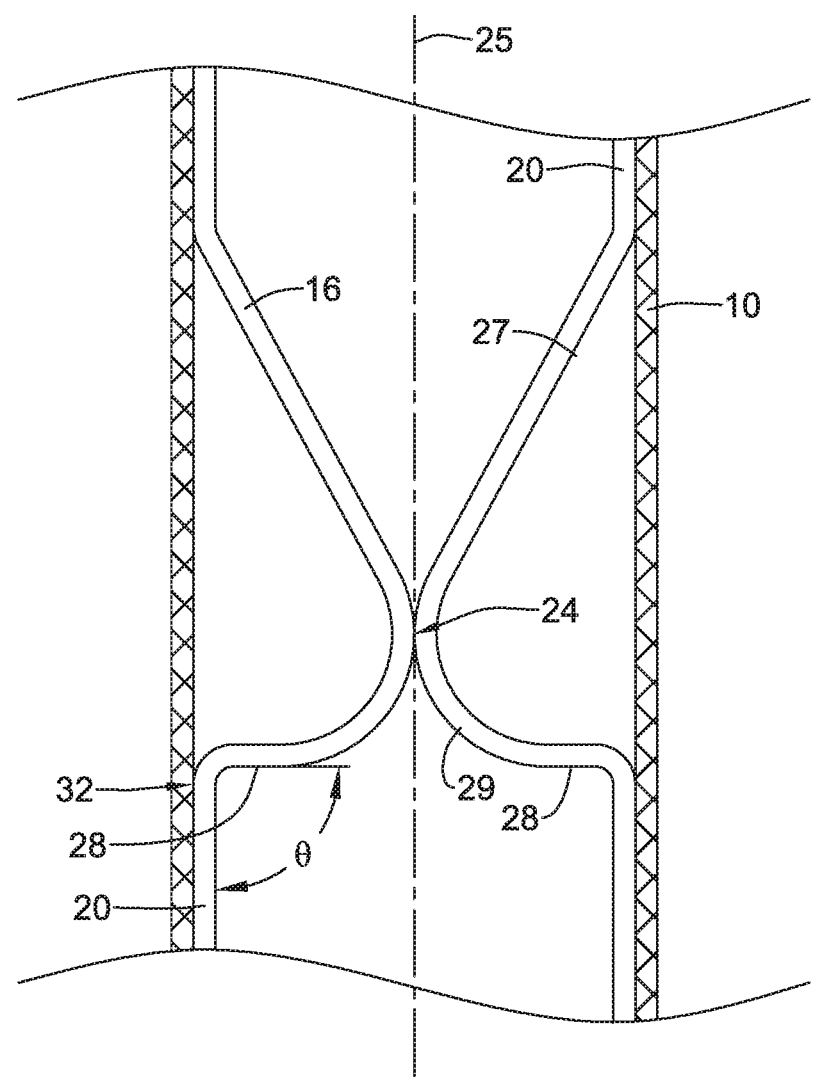
FIG. 10 is a cross-sectional view of another example stent and valve configuration.
Figure 11:
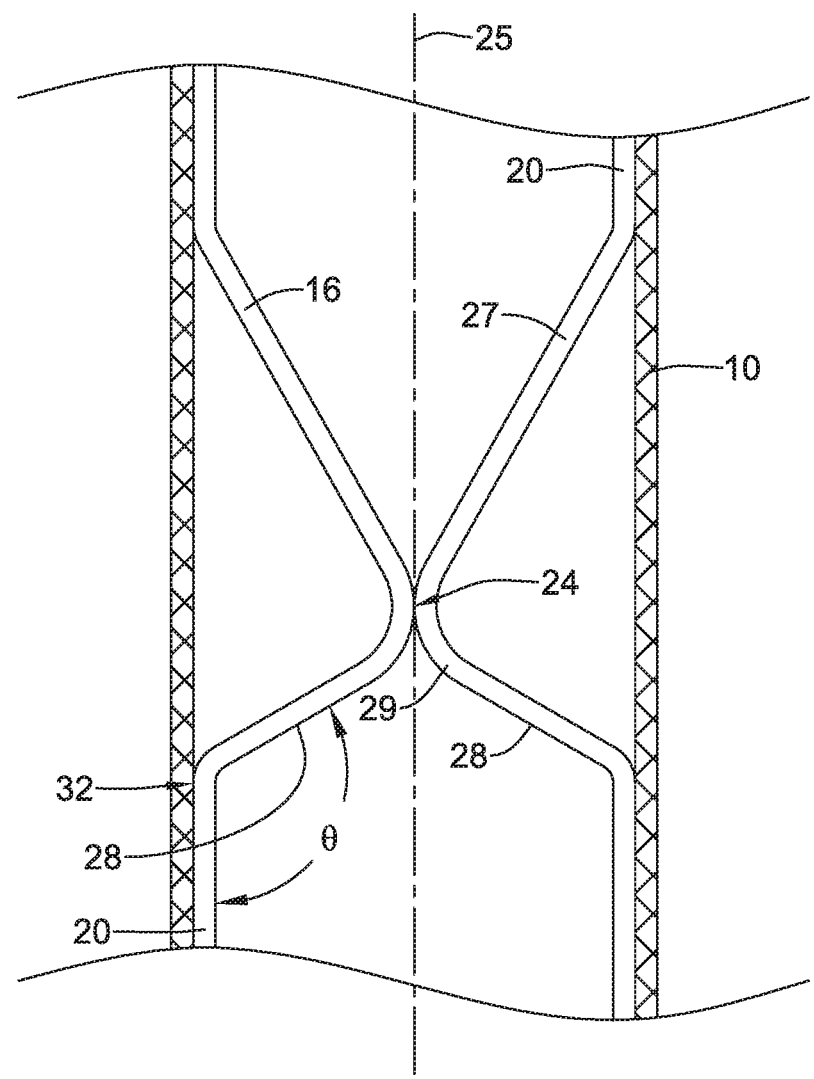
FIG. 11 is a cross-sectional view of another example stent and valve configuration.

FIGS. 9-11 illustrate several of a variety of possible shapes for an example valve 16. It is noted that conical wall portion 27 may taper distally to central longitudinal axis 25 at any desired angle. Additionally, downward-facing portion 28 may extend toward central longitudinal axis 25 from the tubular wall of stent 10 at any desired angle. In some examples, such as those shown in FIGS. 9-11, the trajectory of downward-facing portion 28 of valve 16 may be characterized by defining an angle θ extending between a line drawn tangent to downward-facing portion 28 and stent 10.

For example, FIG. 9 shows angle θ to be an acute angle taken from the surface defined by stent member 10 which is below (distal of) detachment point 32. In other words, angle θ shown in FIG. 9 extends less than 90° from the surface defined by stent member 10 which is below (distal of) detachment point 32. Thus, downward-facing portion 28 may extend distally from detachment point 32 as downward-facing portion 28 extends toward central longitudinal axis 25. Further, it can be seen from FIG. 9 that rounded portion 29 of valve 16 may extend below (distal of) the detachment point 32.

FIG. 10 shows angle θ to be an angle generally perpendicular to the surface defined by stent member 10 which is below (distal of) detachment point 32. In other words, angle θ shown in FIG. 10 extends approximately 90° from the surface defined by stent member 10 which is below detachment point 32. Thus, downward-facing portion 28 may extend perpendicular to central longitudinal axis 25 from detachment point 32 as downward-facing portion 28 extends toward central longitudinal axis 25. Further, it can be seen from FIG. 10 that rounded portion 29 of valve 16 may not extend below the detachment point 32.

FIG. 11 shows angle θ to be an obtuse angle taken from the surface defined by stent member 10 which is below (distal of) detachment point 32. In other words, angle θ shown in FIG. 11 extends greater than 90° from the surface defined by stent member 11 which is below (distal of) detachment point 32. Thus, downward-facing portion 28 may extend proximally from detachment point 32 as downward-facing portion 28 extends toward central longitudinal axis 25. Further, it can be seen from FIG. 11 that rounded portion 29 of valve 16 may extend above (proximal of) the detachment point 32.

In some examples, stent 16 may include one or more surface textures, patterns, micro-patterns, micro-texture, roughened-surfaces, ridges or the like designed and/or configured to prevent or impede material from moving through valve 16 in an retrograde direction (i.e., toward the mouth of the patient). Specifically, it may be desirable to include a surface texture along a portion of valve 16 which prevents material (e.g., stomach acids) from migrating from a patient's stomach, through an example valve, and to a patient's esophagus proximal of the valve 16 and stent 10.

Figure 12:
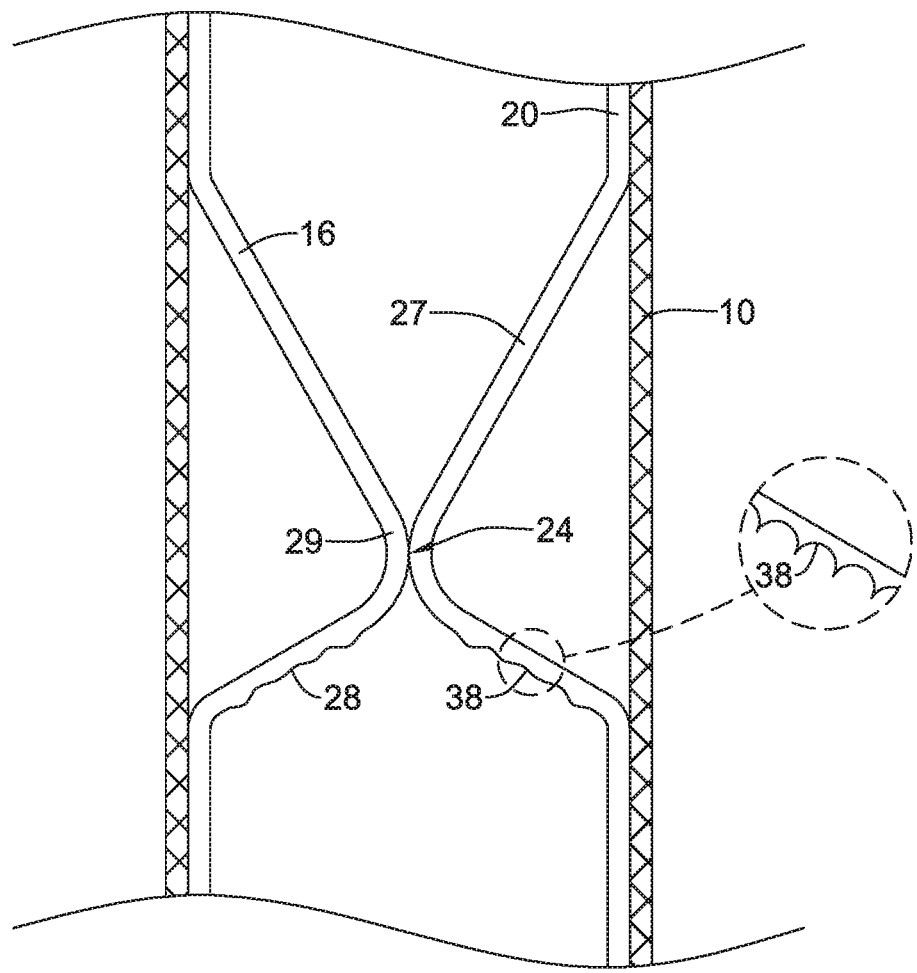
FIG. 12 is a cross-sectional view of another example valve within a stent having a surface texture.

FIG. 12 shows example stent 10 including example valve 16. Further, FIG. 12 shows a surface texture 38 positioned along the downward-facing portion 28 of valve 16. It can be appreciated that surface texture 38 may be positioned such that it is the first portion of valve 16 which may be contacted by material migrating from the stomach. It can be further appreciated that the surface texture 38 may include elements and/or shapes configured to alter the flow of material migrating upward from the stomach. For example, surface texture 38 may include points, tips, indents, cavities, holes, hooks, protrusions, etc., or any combinations thereof. Surface texture 38 may be configured to prevent retrograde movement of stomach acid, etc. from moving proximally along the surface of downward-facing portion 28 of valve 12. Further, in some examples surface texture 38 may be located on other portions of valve 16 and/or stent 10. For example, surface texture 38 may be positioned on rounded portion 29 and/or tapered portion 27. In some instances, the surface texture may include a textured silicone.

Further, in some instances it may be desirable to include a coating on one or more portions of stent 10 (including example valve 16). The coating may be configured to aid the passage of material through valve 16. For example, the coating may reduce the surface friction of one or more portions of valve 16. In other words, the coating may make the surface of valve 16 that contacts material more slippery. In some instances, the coating may include silicone.

In other examples, either the surface texture (described above) or the surface coating (described above) may include hydrophilic elements (e.g., hydrophilic surface texture) or may also include micro-beads (e.g., micro-bead surface texture). In some examples, the micro-beads may be filled with acid neutralizers.

As discussed above, inner layer 20 may define valve 16. Further, inner layer 20 may define a wall thickness of one or more portions of valve 16. As stated above, the wall thickness defined by inner layer 20 may remain substantially uniform along stent 10 (including the portion of inner layer 20 defining valve 16). However, in some instances the thickness of inner layer 20 may vary along stent 10. For example, in some instances one portion of the wall thickness defining valve 16 may be different than another portion of the wall thickness defining valve 16.

Figure 13:
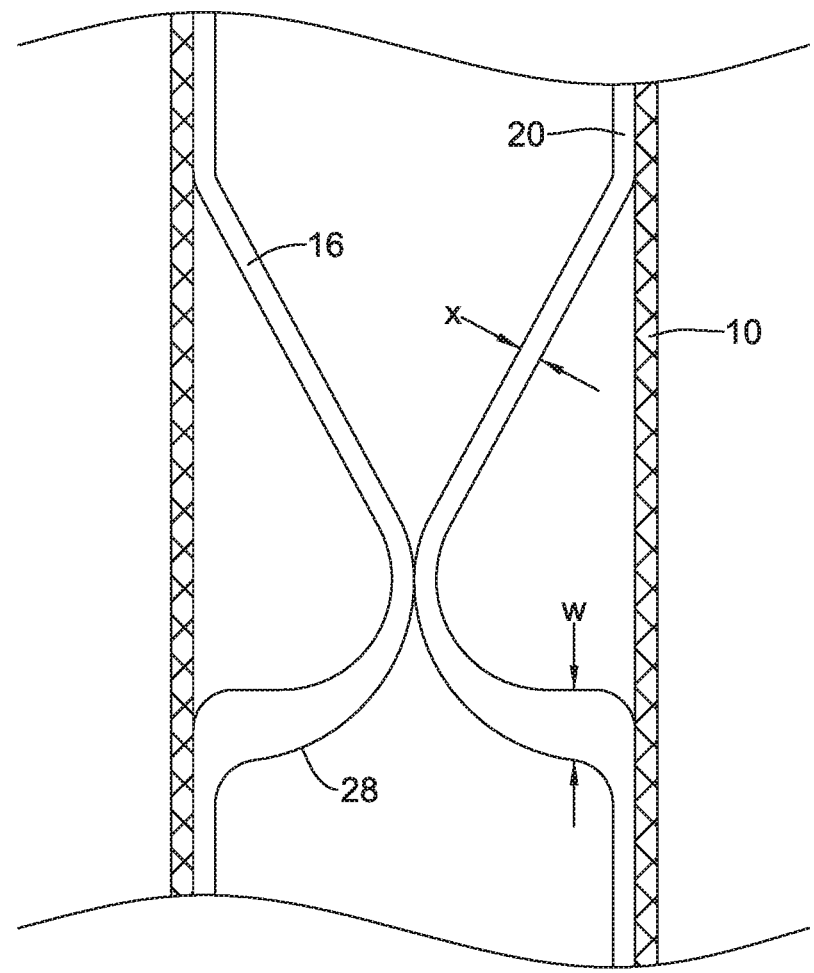
FIG. 13 is a cross-sectional view of another example valve within a stent having a variable wall thickness.

FIG. 13 shows a first portion of valve 16 including a wall thickness depicted as "X." Further, FIG. 13 shows a second portion of valve 16 including a wall thickness depicted as "W." In some instances, wall thickness "W" is thicker than wall thickness "X." Additionally, in some instances it may be desirable to include a thicker portion of valve 16 along downward-facing portion 28 of valve 16. However, this is not intended to be limiting. As such, gravity pulling down on thicker portion of valve along downward-facing portion 28 of valve 16 may tend to close valve 16. It is contemplated in some examples that any portion of valve 16 may include a wall thickness that is thicker (or different) from another portion.

Figure 14:
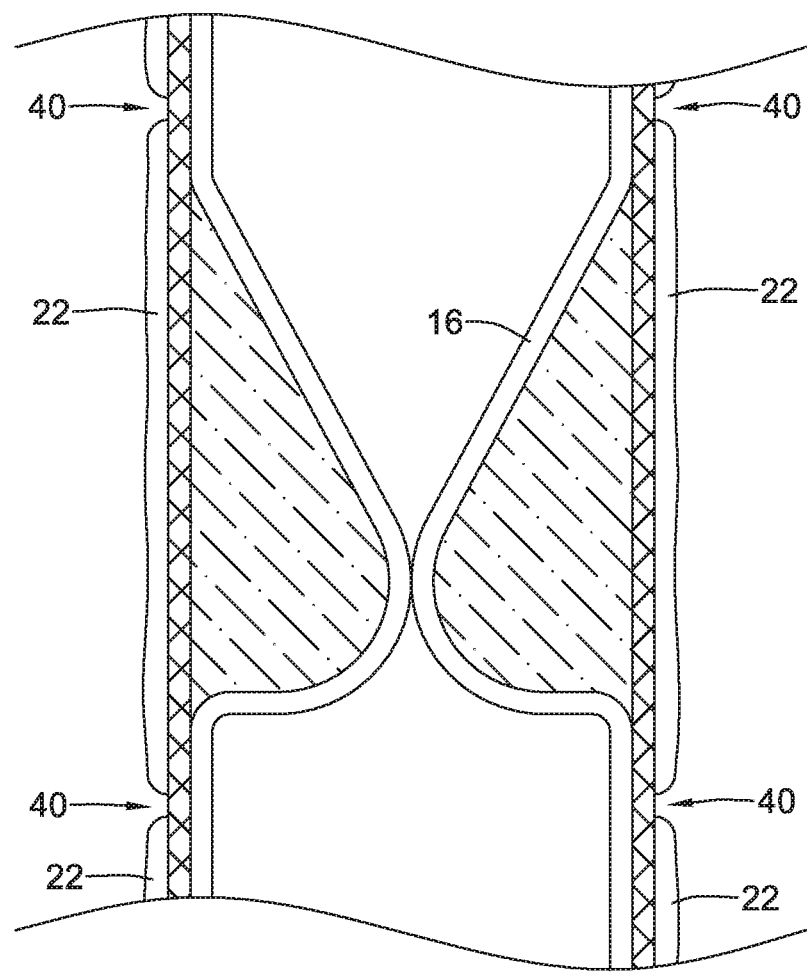
FIG. 14 is a cross-sectional view of another example stent including a valve.

In some examples, stent 16 may include anti-migration elements. Anti-migration elements may include openings, flares, fins, micro-patterns, controlled ingrowth features, quills, or the like. Anti-migration features may be beneficial in controlling the amount stent 16 moves during and/or after deployment in the body lumen. In some instances, one or more portions of stent 10 may include openings configured to allow cellular in-growth into the openings or interstices between stent struts. Cellular ingrowth may prevent stent migration. FIG. 14 shows stent 10 including openings 40 in outer layer 22 configured to permit tissue in-growth therein. FIG. 14 shows four example openings 40 extending through outer layer 22. It is also contemplated that stent 10 may include openings in inner layer 20 coinciding with openings in outer layer 22. However, it is contemplated that more or less than four openings may be included on outer layer 22 and/or inner layer 20. Additionally, it is contemplated that openings 40 may extend and be aligned through outer layer 22, openings or interstices of the wall of stent 10 and inner layer 20.

In some examples, the inner layer 20 and/or outer layer 22 may be applied by spraying, dipping, spinning or attaching a polymer material on the inner and/or outer surface of stent 10. In some examples, the covering may cover the stent filaments 14. Further, as described above, the inner layer 20 and/or outer layer 22 may extend between one or more openings, cells or interstices extending between adjacent stent filaments 14.

Figure 15:
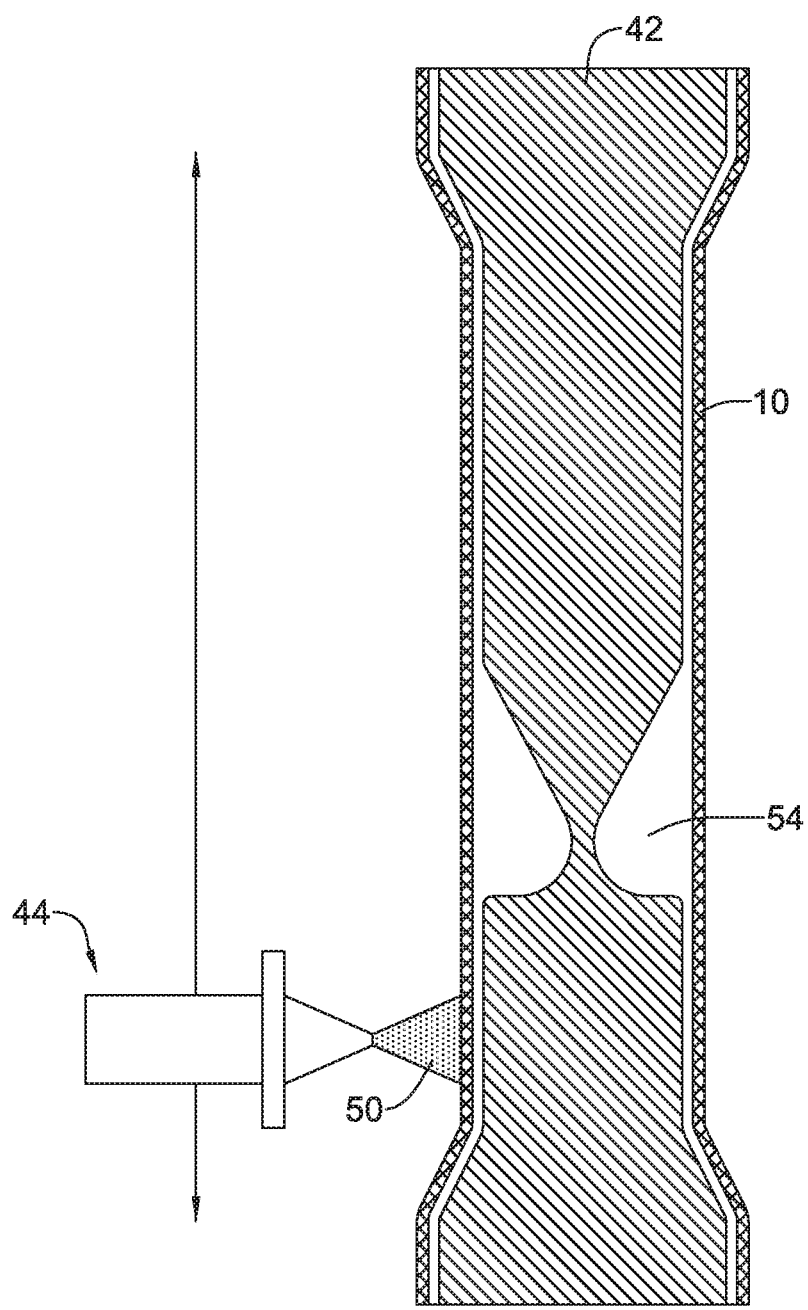
FIGS. 15-17 illustrate an example manufacturing method for forming a valve within an example stent.

FIG. 15 shows an example method for constructing the inner layer 20 within stent 10. As shown in FIG. 15, a mandrel 42 may be inserted into lumen of stent 10. It can be appreciated that mandrel 42 may be a variety of shapes and/or configurations. For example, mandrel 42 may be a generally cylindrical member, which in some instances may include first and/or second flared end regions configured to form flared end regions of the stent 10. Further, it can be appreciated that the shape of mandrel 42 may define the shape of inner layer 20. For example, FIG. 15 shows spraying element 44 applying a spray 50 to stent 10 and mandrel 42 extending within lumen of stent 10. It can be appreciated that spray 50 may pass through the cells of stent member 10, forming a layer of material on the inner surface of stent 10 and/or on mandrel 42. The layer of material applied to inner surface of stent 10 and/or mandrel 42 may correspond to inner layer 20 described in the examples above. Further, as shown in FIG. 15, spraying element 44 may translate the full length of stent 10 while rotating stent 10 and mandrel 42 together, depositing material corresponding to inner layer 20 accordingly.

Additionally, FIG. 15 shows mandrel 42 including one or more recessed portions 54. Recessed portion 54 may extend circumferentially around the entire circumference of mandrel 42. Recessed portions 54 may facilitate formation of one or more portions of inner layer 20 that extend radially inward from the inner surface of stent member 10. Accordingly, the shape/contour of inner layer 20 forming the valve 16 may be determined by the profile of the surface of recessed portion 54. FIG. 15 shows that in some instances, the outer surface of mandrel 42 will be positioned and/or aligned substantially "flush" with the inner surface of stent 10. Depositing layer 50 along portions of mandrel 42 which are substantially flush with the interior surface of stent 10 may cause inner layer 20 to adhere to and/or form an integral interface with the inner surface of stent member 10.

However, applying spray 50 along portions of mandrel 50 which are not substantially flush with the interior surface of stent 10 (e.g., recessed portions 54) may result in spray 50 passing through the cell openings of stent 10 and being deposited along the surface of recessed portions 54 of mandrel 42. It can be appreciated that the recessed portions 54 of mandrel 42 may allow space for spray 50 to extend radially inward beyond the inner surface of stent 10 such that the inner layer 20 is not contacting the stent 10 throughout recessed portion 54. It can be further appreciated from FIG. 15 that inner layer 20 applied along surface of recessed portions 54 may, therefore, form the radially inward extending portions of valve 16.

Figure 16:
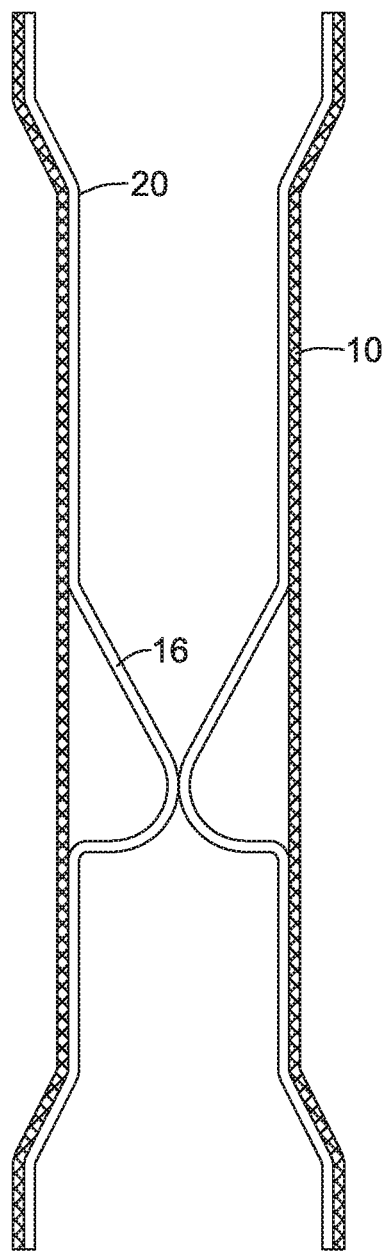

FIG. 16 shows stent 10 after manufacturing mandrel 42 (e.g., mandrel 42 described with respect to FIG. 15) has been removed. It can be appreciated that valve 16 may be formed from a deflectable and/or compressible material which would deform as mandrel 42 is removed from stent 10. In other words, after valve 16 has been constructed according to the manufacturing method described with respect to FIG. 15, mandrel 42 may be removed by pulling it longitudinally through the lumen of stent 10. The flexibility of valve 16 may permit mandrel 42 to be removed accordingly. As shown in FIG. 16, stent 10 including inner layer 20 may be include all the features and/or elements described with respect to FIGS. 1-14 above.

Figure 17:
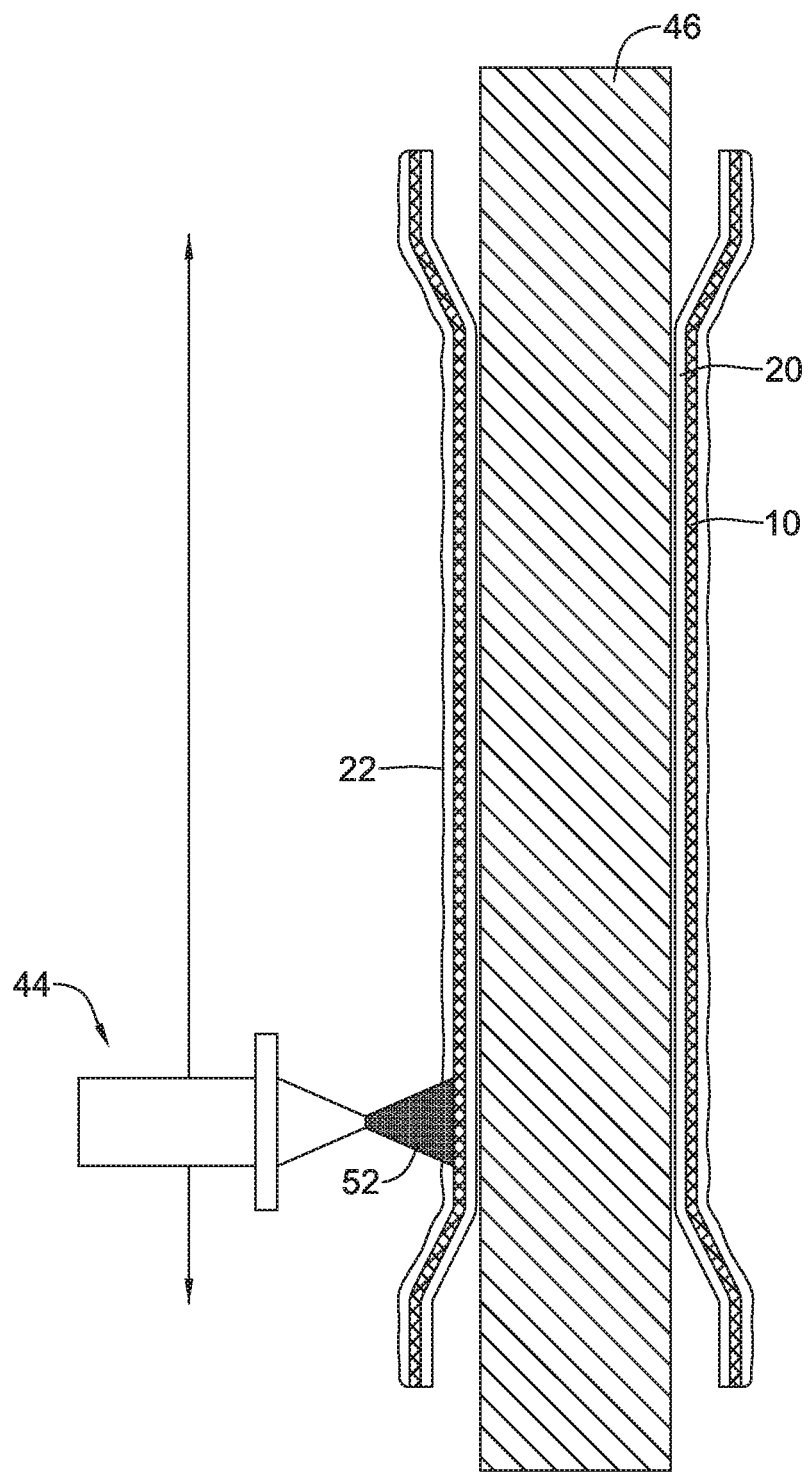

FIG. 17 shows an example method for constructing and/or forming the outer layer 22 of the stent 10 described with respect to FIGS. 1-14 above. As illustrated in FIG. 17, a second manufacturing mandrel 46 may be inserted into stent 10. The second mandrel 46 may not include a annular recess, thus pushing inner layer 20 forming valve 16 radially outward. In some examples, mandrel 46 may be configured such that it forces the inner layer 20 (the construction of which is described with respect to FIGS. 15 and 16 above) radially outward and substantially aligns inner layer 20 along the inner surface of stent 10. In particular, mandrel 46 may force the valve portion 16 (which extends radially inward from the inner surface of stent 10) to align with the portion of inner layer 20 affixed to the inner surface of stent 10.

Additionally, FIG. 17 shows spraying element 44 applying a spray 52 to the outer surface of stent 10. The layer of material applied to the outer surface of stent 10 may correspond to outer layer 22 described in the examples above. Further, as shown in FIG. 17, spraying element 44 may translate the full length of stent 10 while rotating stent 10 and mandrel 46 together, depositing material corresponding to outer layer 22 accordingly.

In some examples, a portion of inner layer 20 may be masked or treated prior to the application of spray 52 (corresponding to outer layer 22). For example, in some instances the portion of inner layer 20 corresponding to valve 16 (i.e., the circumferential portion between first detachment point 30 and second detachment point 32 may be masked or treated (e.g., a talc applied to portion of inner layer 20) such that it does not adhere to the inner surface of stent 10 and/or outer layer 22 while the outer layer 22 is being deposited along stent 10. However, circumferential portions of outer layer 22 proximal of first detachment point 30 and distal of second detachment point 32 may adhere to inner layer 20 and/or stent 10, thus forming a circumferential chamber 26 between inner layer 20 and outer layer 22 spanning the longitudinal distance between the first and second detachment points 30/32.

Figure 18:
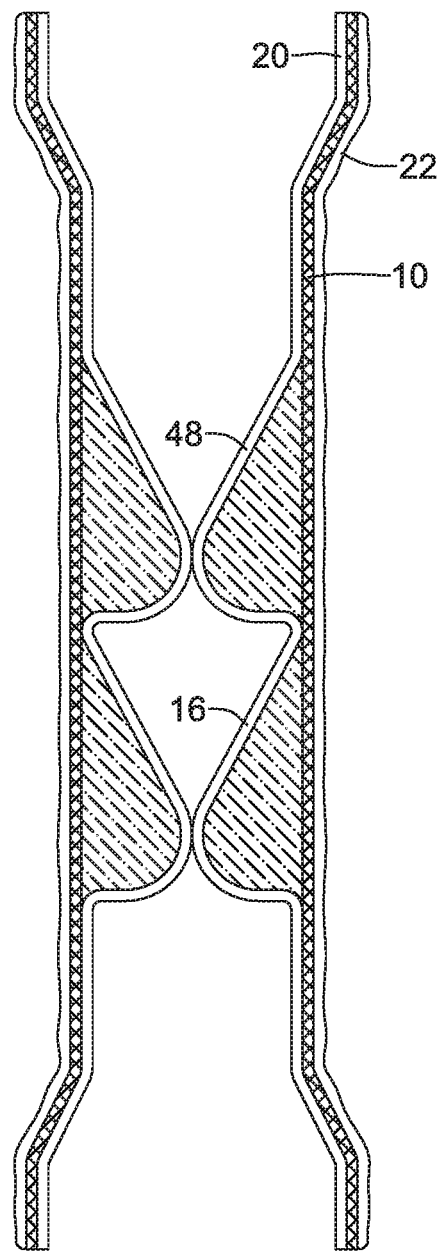
FIG. 18 is a cross-sectional view of another example stent including multiple valves.

In some embodiments, the stent 10 may include a plurality of valves. For example, FIG. 18 shows an example stent 10 including two valves 16/48. It can be appreciated that valves 16/48 may have the same shape or they may have different shapes. Further, valves 16/48 may be positioned along any portion of stent member 10. For example, valves 16/48 may be spaced farther apart than illustrated in FIG. 18. Additionally, one or more of valves 16/48 may incorporate any of the features and/or elements of any of the example stents disclosed herein.

In some examples it may be desirable to include one or more therapeutic agents designed to alleviate and/or mitigate discomfort from acid reflux. For example, any of the examples disclosed herein may include a coating including an acid neutralizer intended to neutralize stomach acids in the esophagus. For example, the down-facing portion of the valve may include a coating including an acid neutralizer. Stomach acids escaping from the stomach may be neutralized when they come into contact with the acid neutralizer.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A method of manufacturing an expandable stent, the method comprising:
   positioning a mandrel within a lumen of a tubular scaffold, the tubular scaffold including an inner surface, an outer surface and a plurality of filaments extending from a first end of the tubular scaffold to a second end of the tubular scaffold, wherein the plurality of filaments are arranged to define a plurality of apertures therebetween, the plurality of apertures extending from the inner surface to the outer surface through a wall of the scaffold and wherein the mandrel includes a recessed portion extending radially inward from an outer surface of the mandrel;
   depositing a material through the apertures of the tubular scaffold such that the material contacts the recessed portion of the mandrel radially inward of the inner surface of the tubular scaffold, wherein depositing the material further includes forming an inner layer of material within the lumen of the scaffold, wherein a portion of the inner layer of material has an outer surface spaced radially inward of and spaced away from and not in contact with the inner surface of the scaffold, wherein the portion of the inner layer of material that is spaced radially inward of and spaced away from the inner surface of the scaffold forms a valve extending radially inward from the inner surface of the scaffold, wherein the valve is formed in a middle region of the tubular scaffold with first and second end regions of the tubular scaffold extending axially away from opposite ends of the valve such that the valve is located between the first and second end regions of the tubular scaffold; and
   removing the mandrel.

2. The method of claim 1, wherein depositing material through the apertures of the tubular scaffold further comprises depositing the inner layer of material on the inner surface of the scaffold between a first circumferential location and a first end of the scaffold and between a second circumferential location and a second end of the scaffold.

3. The method of claim 2, further comprising depositing an outer layer of material along the outer surface of the scaffold and extending across the apertures between the first circumferential location and the second circumferential location.

4. The method of claim 2, further comprising depositing an outer layer of material along the outer surface of the scaffold from the first end of the scaffold to the second end of the scaffold.

5. The method of claim 4, wherein the inner layer is circumferentially attached to the outer layer at the first circumferential location and the inner layer is circumferentially attached to the outer layer at the second circumferential location to form an annular chamber.

6. The method of claim 5, wherein the annular chamber extends circumferentially around a central longitudinal axis of the tubular scaffold.

7. The method of claim 6, wherein the annular chamber is bounded by the outer surface of the inner layer of material and an inner surface of the outer layer extending from the first circumferential location to the second circumferential location.

8. The method of claim 7, wherein the valve is configured to shift between a closed configuration and an open configuration.

9. The method of claim 1, wherein the recessed portion of the mandrel is configured to form a surface texture on at least a portion of an inner surface of the inner layer.

10. The method of claim 9, wherein the surface texture is only on a downward facing portion of the inner surface of the valve.

11. The method of claim 10, wherein the surface texture on the inner surface of the valve is opposite the outer surface of the inner layer, the outer surface being devoid of the surface texture.

12. The method of claim 1, depositing a material through the apertures of the tubular scaffold further includes spraying the material through the apertures.

13. A method of manufacturing an expandable stent, the method comprising:
   positioning a mandrel within a lumen of a tubular scaffold, the tubular scaffold including an inner surface, an outer surface and a plurality of filaments extending from a first end of the tubular scaffold to a second end of the tubular scaffold, wherein the plurality of filaments are arranged to define a plurality of apertures therebetween, the plurality of apertures extending from the inner surface to the outer surface through a wall of the scaffold and wherein the mandrel includes a recessed portion extending radially inward from an outer surface of the mandrel, the recessed portion having a radially innermost extent and a radially outermost extent, wherein the inner surface of the scaffold extends linearly along the outermost extent of the recessed portion and does not extend into the recessed portion;

depositing a material along the scaffold from a first circumferential location to a second circumferential location such that the material is deposited to span across the plurality of apertures of the tubular scaffold and deposited along at least a portion of the recessed portion of the mandrel to form a valve having an annular chamber therebetween; and removing the mandrel.

14. The method of claim 13, wherein depositing a material along the scaffold from a first circumferential location to a second circumferential location further includes spraying the material through the apertures.

15. The method of claim 13, wherein the annular chamber is bounded by an outer surface of an inner layer of material formed along the recessed portion and an inner surface of an outer layer spanning the plurality of apertures of the tubular scaffold.

16. The method of claim 13, wherein the recessed portion of the mandrel is configured to form a surface texture only on a downward facing portion of an inner surface of the valve.

17. A method of manufacturing an esophageal stent, the method comprising:

positioning a mandrel within a lumen of a tubular scaffold, the tubular scaffold including a plurality of filaments arranged to define a plurality of apertures extending through a wall of the scaffold, and wherein the mandrel includes a first end, a second end, a middle region extending therebetween, the middle region including an outer surface and a recessed portion disposed in the middle region and extending radially inward from the outer surface of the middle region;

depositing a first layer of material through the plurality of apertures onto a surface of the recessed portion of the mandrel;

depositing a second layer of material on at least a portion of an outer surface of the tubular scaffold;

wherein an outer surface of the first layer of material deposited onto the surface of the recessed portion of the mandrel is spaced away from an inner surface of the second layer of material to form a valve having an annular chamber therebetween, thereby forming the valve in the middle region with a first end region of the tubular scaffold extending beyond the valve to the first end of the mandrel and a second end region of the tubular scaffold extending beyond the valve to the second end of the mandrel; and removing the mandrel.

18. The method of claim 17, wherein the tubular scaffold does not extend into the recessed portion of the mandrel.

19. The method of claim 18, wherein depositing the first layer of material includes spraying the first layer of material through the apertures.

20. The method of claim 13, wherein the mandrel includes first and second flared end regions and a middle region extending therebetween, and the recessed portion extends radially inward from the outer surface of the mandrel in the middle region, wherein depositing the material along the scaffold forms the valve in the middle region.

* * * * *